United States Patent [19]

Abiko et al.

[11] Patent Number: 4,845,100

[45] Date of Patent: Jul. 4, 1989

[54] CARBOSTYRIL DERIVATIVES AND SALTS THEREOF, PROCESSES FOR PREPARING THE SAME AND CARDIOTONIC COMPOSITION CONTAINING THE SAME

[75] Inventors: Atsushi Abiko, Cambridge, Mass.; Takafumi Fujioka, Tokushima, Japan; Kazuyuki Nakagawa, Tokushima, Japan; Kazumi Kondo, Tokushima, Japan

[73] Assignee: Otsuka Pharmaceutical Co., Ltd., Tokyo, Japan

[21] Appl. No.: 850,815

[22] Filed: Apr. 10, 1986

[30] Foreign Application Priority Data

Apr. 12, 1985 [JP] Japan ................................. 60-78980
Oct. 11, 1985 [JP] Japan ............................... 60-227493
Mar. 24, 1986 [JP] Japan ................................. 61-66889

[51] Int. Cl.$^4$ .................. A61K 31/495; C07D 401/04
[52] U.S. Cl. ..................................... 514/253; 544/363
[58] Field of Search ......................... 544/363; 514/253

[56] References Cited

U.S. PATENT DOCUMENTS

| | | | |
|---|---|---|---|
| 4,022,776 | 5/1977 | Nakagawa et al. | 544/363 |
| 4,022,784 | 5/1977 | Nakagawa et al. | 544/363 |
| 4,026,897 | 5/1977 | Nakagawa et al. | 544/363 |
| 4,415,572 | 11/1983 | Tominaga et al. | 544/363 |
| 4,454,130 | 6/1984 | Tominaga et al. | 544/363 |
| 4,468,402 | 8/1984 | Tominaga et al. | 544/363 |
| 4,487,772 | 12/1984 | Tominaga et al. | 514/252 |

FOREIGN PATENT DOCUMENTS 58-148817 9/1983 Japan .
58-148861 9/1983 Japan .

OTHER PUBLICATIONS

"Chemical Abstracts", vol. 98, 1983, col. 98:34510e, (Abstract of Belgium Patent No. 892,148, 8/16/82).
Tominaga et al., "Chemical Abstracts", vol. 106, 198, col. 106(13):102057y, (Abstract of Chem. Pharm. Bull., vol. 34, No. 2, 1986), pp. 682–693.

*Primary Examiner*—Richard L. Raymond
*Assistant Examiner*—James H. Turnipseed
*Attorney, Agent, or Firm*—Finnegan, Henderson, Farabow, Garrett & Dunner

[57] ABSTRACT

Carbostyril derivatives and salts thereof having excellent positive inotropic activity, increasing activity of coronary blood flow, as well as hypotensive activity in one hand, and also they do not have substantially increasing activity of heart beat as their characteristic property, as well as they have less side-effects in the central nervous system, such as they have less vomiting effect, decreasing effect in motor function and tremor effect.

18 Claims, No Drawings

CARBOSTYRIL DERIVATIVES AND SALTS THEREOF, PROCESSES FOR PREPARING THE SAME AND CARDIOTONIC COMPOSITION CONTAINING THE SAME

FIELD OF THE INVENTION

The present invention relates to novel carbostyril derivatives and salts thereof, processes for preparing the same and cardiotonic composition containing the same as the active ingredient.

PRIOR ART

Carbostyril derivatives having some cardiotonic activities are known for example in U.S. Pat. Nos. 4,487,772, 4,415,572 and 4,514,401.

SUMMARY OF THE INVENTION

Carbostyril derivatives and salts thereof according to the present invention are novel compounds which have not been known in any prior art literatures, and they are represented by the general formula (1),

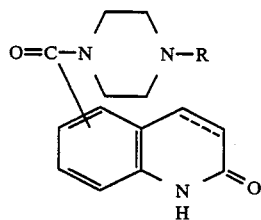

[wherein R is an alkenyl group having 7-12 carbon atoms, a phenyl-lower alkenyl group which may have, on the phenyl ring, lower alkylthio groups or lower alkylsulfinyl groups as the substituents, a phenyl-lower alkynyl group, a phenyl group which may have 1-3 substituents selected from the group consisting of a halogen atom, a lower alkyl group, a lower alkoxy group, a lower alkylthio group and a lower alkylsulfinyl group on the phenyl ring, or a group of the formula

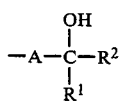

(wherein A is a lower alkylene group; $R^1$ is a hydrogen atom, a lower alkyl group or a phenyl group; and $R^2$ is a phenyl group which may have 1-3 substituents selected from the group consisting of a hydroxy group, a halogen atom, a lower alkyl group, a lower alkoxy group, a lower alkanoylamino group, a lower alkylthio group and a lower alkylsulfinyl group on the phenyl ring); the carbon-carbon bond between 3- and 4-positions in the carbostyril skeleton is a single or double bond].

The carbostyril derivatives and salts thereof represented by the general formula (1) according to the present invention possess increasing activity of the heart muscle contraction (positive inotropic activity), increasing activity of coronary blood flow, hypotensive activity and antiinflammatory activity, thus they are useful as cardiotonic agents for curing various heart diseases such as congestional cardiac insufficiency, mitral valvular disease, artrial fibrillation, artrial flutter, paroxysmal artrial trachycardia and the like, as well as they are useful as antiinflammatory agents. Specifically, carbostyril derivatives or salts thereof represented by the general formula (1) according to the present invention possess excellent positive inotropic activity, increasing activity of coronary blood flow, as well as hypotensive activity in one hand, also they do not substantially have increasing activity of heart beat as their characteristic property. Additionally, said carbostyril derivatives and salts thereof are very stable compounds, thus they have features that they can easily be handled in preparing pharmaceutical compositions in desired forms. Furthermore, said carbostyril derivatives and salts thereof according to the present invention are characterized in that they have less side-effects in central nervous system, such as they have less vomiting effect, decreasing effect in motor function, tremor effect and the like as their side-effects.

An object of the present invention is to provide novel carbostyril derivatives and salts thereof represented by the general formula (1).

Another object of the present invention is to provide processes for preparing the carbostyril derivatives and salts thereof.

Further object of the present invention is to provide cardiotonic compositions containing the carbostyril derivative and salt thereof as the active ingredient.

DETAILED DESCRIPTION OF PREFERRED EMBODIMENTS

In carbostyril derivatives and salts thereof represented by the general formula (1), examples of the substituents which are defined in the symbols of A and R are shown as follows.

As to the lower alkylene group, a straight-chain or branched-chain alkylene group having 1-6 carbon atoms, for examples methylene, ethylene, trimethylene, 2-methyltrimethylene, 2,2-dimethyltrimethylene, 1-methyltrimethylene, methylmethylene, ethylmethylene, tetramethylene, pentamethylen, hexamethylene and the like can be exemplified.

As to the halogen atom, a fluorine atom, a chlorine atom, a bromine atom and an iodine atom can be exemplified.

As to the lower alkyl group, a straight-chain or branched-chain alkyl group having 1-6 carbon atoms, for example, methyl, ethyl, propyl, isopropyl, butyl, tertbutyl, pentyl and hexyl groups and the like can be exemplified.

As to the lower alkoxy group, a straight-chain or branched-chain alkoxy group having 1-6 carbon atoms, for example, methoxy, ethoxy, propoxy, isopropoxy, butoxy, tert-butoxy, pentyloxy and hexyloxy groups and the like can be exemplified.

As to the alkenyl group having 7-12 carbon atoms, a straight-chain or branched-chain alkenyl group having 7-12 carbon atoms, and having 1-3 double bonds in the chain, for example, 1-heptenyl, 1-octenyl, 1-nonenyl, 1-decenyl, 1-undecenyl, 1-dodecenyl, 1-heptenyl, 3-heptenyl, 2-methyl-4-heptenyl, 2-methyl-5-heptenyl, 4-methyl-2-heptenyl, 3-methyl-1-heptenyl, 1,3-heptadienyl, 1,4-heptadienyl, 1,5-heptadienyl, 1,6-heptadienyl, 2,4-heptadienyl, 2-methyl-2,4-heptadienyl, 2,6-dimethyl-2,4-heptadienyl, 2,5-dimethyl-1,3-heptadienyl, 2,4,6-trimethyl-2,4-heptadienyl, 2-octenyl, 3-octenyl, 4-octenyl, 2-methyl-5-octenyl, 2-methyl-6-octenyl, 2-methyl-6-octenyl, 2-methyl-6-octenyl, 2-methyl-7-octenyl, 1,3-octadienyl, 1,4-octadienyl, 1,5-octadienyl, 1,6- octadienyl, 1,7-octadienyl, 2,4-octadienyl, 3,7-octadienyl, 4,8-dimethyl-3,7-octadienyl, 2,4,6-trimethyl-3,7-octadienyl, 3,4-dimethyl-2,5-octadienyl, 4,8-dimethyl-2,6-octadienyl, 2-nonenyl, 3-nonenyl, 4-nonenyl, 2-methyl-5-nonenyl, 2-methyl-6-nonenyl, 2-methyl-7-nonenyl, 2-methyl-8-nonenyl, 1,3-nonadienyl, 1,4-nonadienyl, 1,5-nonadienyl, 1,6-nonadienyl, 1,7-nonadienyl, 1,8-nonadienyl, 2,4-nonadienyl, 3,7-nonadienyl, 4,8-dimethyl-3,7-nonadienyl, 2,4,6-trimethyl-3,7-nonadienyl, 3,4-dimethyl-2,5-nonadienyl, 4,8-dimethyl-2,6-nonadienyl, 2-decenyl, 3-decenyl, 4-decenyl, 5-decenyl, 2-methyl-6-decenyl, 3-methyl-7-decenyl, 4-methyl-8-decenyl, 5-methyl-9-decenyl, 1,3-decadienyl, 1,4-decadienyl, 1,5-decadienyl, 1,6-decadienyl, 1,7-decadienyl, 1,8-decadienyl, 1,9-decadienyl, 2-methyl-2,4-decadienyl, 3-methyl-2,5-decadienyl, 4,8-dimethyl-2,6-decadienyl, 2,4,6-trimethyl-3,7-decadienyl, 2,9-dimethyl-3,7-decadienyl, 2-undecenyl, 3-undecenyl, 4-undecenyl, 5-undecenyl, 2-methyl-6-undecenyl, 3-methyl-7-undecenyl, 4-methyl-8-undecenyl, 5-methyl-9-undecenyl, 2-methyl-10-undecenyl, 1,3-undecadienyl, 1,4-undecadienyl, 1,5-undecadienyl, 1,6-undecadienyl, 1,7-undecadienyl, 1,8-undecadienyl, 1,9-undecadienyl, 1,10-undecadienyl, 2-methyl-2,4-undecadienyl, 3-methyl-2,5-undecadienyl, 4,8-dimethyl-2,6-undecadienyl, 2,4,6-trimethyl-3,8-undecadienyl, 2,9-dimethyl-3,8-undecadienyl, 2-dodecenyl, 3-dodecenyl, 4-dodecenyl, 5-dodecenyl, 6-dodecenyl, 2-methyl-7-dodecenyl, 3-methyl-8-dodecenyl, 4-methyl-9-dodecenyl, 5-methyl-10-dodecenyl, 6-methyl-11-dodecenyl, 2-methyl-2,4-dodecadienyl, 3-methyl-2,5-dodecadienyl, 4,8-dimethyl-2,6-dodecadienyl, 2,4,6-trimethyl-2,7-dodecadienyl, 2,10-dimethyl-2,8-dodecadienyl, 2,5-dimethyl-3,7-dodecadienyl, 4,8,12-trimethyl-3,7,11-dodecatrienyl, 1,3,5-heptatrienyl, 2,4,6-octatrienyl, 1,3,6-nonatrienyl, 2,6,8-decatrienyl and 1,5,7-undecatrienyl groups and the like can be exemplified.

As to the phenyl-lower alkenyl group which may have, on the phenyl ring, lower alkylthio groups or lower alkylsulfinyl groups as the substituents, a phenylalkenyl group in which the alkenyl moiety is a straight-chain or branched-chain alkenyl group having 2-6 carbon atoms, which may have, on the phenyl group, a straight-chain or branched-chain alkylthio group having 1-6 carbon atoms or a straight-chain or branched-chain alkenylsulfinyl group having 1-6 carbon atoms as the substituents, for example, styryl, 3-phenyl-1-propenyl, 3-phenyl-2-propenyl, 4-phenyl-3-butenyl, 4-phenyl-2-butenyl, 5-phenyl-4-pentenyl, 5-phenyl-3-pentenyl, 5-phenyl-2-pentenyl, 6-phenyl-5-hexenyl, 6-phenyl-4-hexenyl, 6-phenyl-3-hexenyl, 6-phenyl-2-hexenyl, 2-methyl-4-phenyl-3-butenyl, 2-methylstyryl, 1-methylstyryl, 2-, 3- or 4-methylthiostyryl, 2-, 3- or 4-ethylthiostyryl, 2-, 3- or 4-propylthiostyryl, 2-butylthiostyryl, 3-(tert-butylthio)styryl, 4-pentylthiostyryl, 3-hexylthiostyryl, 3,5-dimethylthiostyryl, 2,6-dimethylthiostyryl, 3,4-dimethylthiostyryl, 3,4-diethylthiostyryl, 3,4,5-trimethylthiostyryl, 4-methylthiophenyl-3-butenyl, 4-(3-tert-butylthiophenyl)-2-butenyl, 5-(4-hexylthiophenyl)-4-pentenyl, 6-(3,4-dimethylthiophenyl)-5-hexenyl, 3-(2-ethylthiophenyl)-2-propenyl, 6-(4-methylthiophenyl)-3hexenyl, 3-(2-methylsulfinylphenyl)-2-propenyl, 3-(3-ethylsulfinyl)-2-propenyl, 3-(4-methylsulfinylphenyl)-1-propenyl, 4-(3-propylsulfinylphenyl)-3-butenyl, 4-(3-tert-butylsulfinylphenyl)-2-butenyl, 5-(4-hexylsulfinylphenyl)-4-pentenyl and 6-(3,4-dimethylsulfinylphenyl)-5-hexenyl groups and the like can be exemplified.

As to the phenyl-lower alkynyl group, a phenylalkynyl group in which the alkynyl moiety is a straight-chain or branched-chain alkynyl group having 2-6 carbon atoms, for example, 2-phenylethynyl, 3-phenyl-1-propynyl, 3-phenyl-2-propynyl, 4-phenyl-3-butynyl, 4-phenyl-2-butynyl, 5-phenyl-4-pentynyl, 5-phenyl-3-pentynyl, 5-phenyl-2-pentynyl, 6-phenyl-3-hexynyl, 6-phenyl-2-hexynyl, 2-methyl-4-phenyl-3-butynyl, 1-methyl-3-phenyl-2-propynyl and 3-methyl-3-phenyl-1-propynyl groups and the like can be exemplified.

As to the phenyl group which may have 1-3 substituents selected from the group consisting of a halogen atom, a lower alkyl group, a lower alkoxy group, a lower alkylthio group and a lower alkylsulfinyl group; a phenyl group which may have 1-3 substituents selected from the group consisting of a halogen atom, a straight-chain or branched-chain alkyl group having 1-6 carbon atoms, a straight-chain or branched-chain alkoxy group having 1-6 carbon atoms, a straight-chain or branched-chain alkylthio group having 1-6 carbon atoms, and a straight-chain or branched-chain alkylsulfinyl group having 1-6 carbon atoms, for example, phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluoropenyl, 3,5-dibromophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 2-methoxyphenyl, 3-methoxyphenyl, 4methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 3,4,5-trichlorophenyl, 3,4,5-trimethylphenyl, 2,5-dimethoxyphenyl, 2-methylthiophenyl, 3-methylthiophenyl, 4-methylthiophenyl, 2-ethylthiophenyl, 3-ethylthiophenyl, 4-ethylthiophenyl, 3-isopropylthiophenyl, 4-hexylthiophenyl, 3,4-dimethylthiophenyl, 2,5-dimethylthiophenyl, 2-methylsulfinylphenyl, 3-methylsulfinylphenyl, 4-methylsulfinylphenyl, 2-ethylsulfinylphenyl, 3-ethylsulfinylphenyl, 4-ethylsulfinylphenyl, 3-isopropylsulfinylphenyl, 4-hexylsulfinylphenyl, 3,4-dimethylsulfinylphenyl, 2,5-dimethylsulfinylphenyl, 2-methyl-4-chlorophenyl, 2-methyl-3-chlorophenyl and 4-methyl-3-bromophenyl groups and the like can be exemplified.

As to the lower alkylthio group, a straight-chain or branched-chain alkylthio group having 1-6 carbon atoms, for example, methylthio, ethylthio, propylthio, isopropylthio, butylthio, tert-butylthio, pentylthio and hexylthio groups and the like can be exemplified.

As to the lower alkylsulfinyl group, a straight-chain or branched-chain alkylsulfinyl group having 1-6 carbon atoms, for example, methylsulfinyl, ethylsulfinyl, propylsulfinyl, isopropylsulfinyl, butylsulfinyl, tert-butylsulfinyl, pentylsulfinyl and hexylsulfinyl groups and the like can be exemplified.

As to the phenyl group which may have 1-3 substituents selected from the group consisting of a hydroxy group, a halogen atom, a lower alkyl group, a lower alkoxy group, a lower alkanoylamino group, a lower alkylthio group and a lower alkylsulfinyl group on the phenyl ring, a phenyl group which may have 1-3 substituents selected from the group consisting of a hydroxy group, a halogen atom, a straight-chain or branched-chain alkyl group having 1-6 carbon atoms, a straight-chain or branched-chain alkoxy group having 1-6 carbon atoms, a straight-chain or branched-chain alkanoylamino group having 1-6 carbon atoms, a straight-chain or branched-chain alkylthio group having 1-6 carbon atoms, and a straight-chain or branched-chain alkylsulfinyl group having 1-6 carbon atoms on the phenyl ring, for example, phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 2,4,5-trichlorophenyl, 3,4,5-trimethylphenyl, 2,5-dimethoxyphenyl, 2-methylthiophenyl, 3-methylthiophenyl, 4-methylthiophenyl, 2-ethylthiophenyl, 3-ethylthiophenyl, 4-ethylthiophenyl, 3-isopropylthiophenyl, 4-hexylthiophenyl, 3,4-dimethylthiophenyl, 2,5-dimethylthiophenyl, 2-methylsulfinylphenyl, 3-methylsulfinylphenyl, 4-methylsulfinylphenyl, 2-ethylsulfinylphenyl, 3-ethylsulfinylphenyl, 4-ethylsulfinylphenyl, 3-isopropylsulfinylphenyl, 4-hexylsulfinylphenyl, 3,4-dimethylsulfinylphenyl, 2,5-dimethylsulfinylphenyl, 2-methyl-4-chlorophenyl, 2-methyl-3-chlorophenyl, 4-methyl-3-bromophenyl, 2-hydroxyphenyl, 3-hydroxyphenyl, 4-hydroxyphenyl, 2,4-dihydroxyphenyl, 3,4-dihydroxyphenyl, 3,4,5-trihydroxyphenyl, 2-acetylaminophenyl, 3-propionylaminophenyl, 4-formylaminophenyl, 2-butyrylaminophenyl, 3-pentanoylaminophenyl and 4-hexanoylaminophenyl groups and the like can be exemplified.

As to the lower alkanoylamino group, a straight-chain or branched-chain alkanoyl-substituted amino group having 1-6 carbon atoms, for example, formylamino, acetylamino, propionylamino, butyrylamino, isobutyrylamino, pentanoylamino, tert-butylcarbonylamino and hexanoylamino groups and the like can be exemplified.

Carbostyril derivatives and salts thereof represented by the general formula (1) can be prepared by the following reaction process formulas.

Reaction process formula - 1

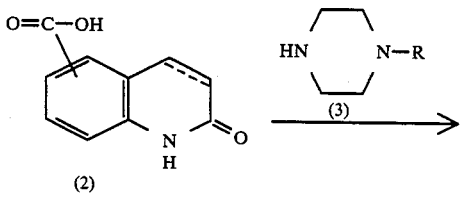

(2)

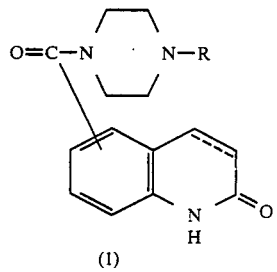

(1)

[wherein R and the carbon-carbon bond between 3- and 4-positions in the carbostyril skeleton are the same as defined above].

Above-mentioned reaction process formula 1 can be carried out by methods commonly used in amido-bond formation reaction in which a carbostyril derivative or a carbostril derivative of its carboxy group is activated represented by the general formula (2) is reacted with an amine or an amine in which the amino group is activated represented by the general formula (3). As to the amidobond formation reactions, the following methods can be exemplified:

(a) A mixed acid anhydroride method, that is a method by reacting a carbostyril derivative of the general formula (2) with an alkylhalocarboxylic acid to prepare a corresponding mixed acid anhydride, then futher reacting said mixed acid anhydride with an amine of the general formula (3).

(b) An activated ester method, that is a method by converting a carbostyril derivative of the general formula (2) into an activated ester, for example, p-nitrophenyl ester, N-hydroxysuccinimide ester 1-hydroxybenzotriazole ester or the like, then reacting said activated ester with an amine of the general formula (3).

(c) A carbodiimide method, that is a method by condensing a carbostyril derivative of the general formula (2) with an amine of the general formula (3) in the presence of an activating agent, for example dicyclohexylcarbodiimide, carbonyldiimidazole or the like.

(d) Other methods, for example:

(d-1) A method by reacting a carboxylic anhydride prepared by reacting a carbostyril derivative of the general formula (2) with a dehydrating agent such as acetic anhydride, then reacting said carboxylic anhydride with an amine of the general formula (3).

(d-2) A method by reacting an ester prepared by reacting a carbostyril derivative of the general formula (2) with a lower alcohol, then reacting said ester with an amine of the general formula (3) at an elevated temperature under pressure.

(d-3) A method by reacting a carboxylic acid halide prepared by reacting a carbostyril derivative of the general formula (2) with an acid halide, then reacting said carboxylic acid halide with an amine of the general formula (3).

(d-4) A method by reacting an activated carbostyril derivative of the general formula (2) prepared by activating it with a phosphorus compound such as triphenylphosphine, diethyl cyanophosphate, diethyl chlorophosphate and the like, then said activated carbostyril derivative is reacted with an amine of the general formula (3).

In carrying out of the above-mentioned method (a), a mixed acid anhydride method, the mixed acid anhydride can be prepared by a conventional Schotten-Baumann reaction, and the desired product of the general formula (1) can be prepared by reacting the intermediate product, without separating from the reaction mixture, with an amine of the general formula (3). The Schotten-Baumann reaction is generally carried out in the presence of a basic compound conventionally used in Schotten-Baumann reaction, for example, an organic base such as triethylamine, trimethylamine, pyridine, dimethylaniline, N-methylmorpholine, 4-dimethylaminopyridine, 1,5-diazacyclo [4,3,0]nonene-5 (DBN), 1,8-diazabicyclo[5,4,0]undecene-7 (DBU), 1,4-diazabicyclo[2,2,2]octane (DABCO) or the like, or an inorganic base such as potassium carbonate, sodium carbonate, potassium bicarbonate, sodium bicarbonate or the like, at about $-20°$ to $100°$ C., preferably at $0°$ to $50°$ C. by taking about 5 minutes to 10 hours, preferably by taking about 5 minutes to 2 hours. The reaction between the prepared mixed acid anhydride with an amine of the general formula (3) is carried out at about $-20°$ to $150°$ C., preferably at about $10°$ to $50°$ C., by taking about 5 minutes to 10 hours, preferably by taking about 5 minutes to 5 hours. The above-mentioned mixed acid anhydride method (a) may be carried out without or in a suitable solvent which is conventionally used in such type of mixed acid anhydride method, specifically, for example a halogenated hydrocarbon such as methylene chloride, chloroform, dichloroethane or the like; an aromatic hydrocarbon such as benzene, toluene, xylene or the like; an ether such as diethyl ether, tetrahydrofuran, dimethoxyethane or the like, an ester such as methyl actate, ethyl acetate or the like; an aprotic polar solvent such as N,N-dimethylformamide, dimethyl sulfoxide, hexamethylphosphoric triamide or the like. As to the alkylhalocarboxylic acid used in the above-mentioned mixed acid anhydride method, methyl chloroformate, methyl bromoformate, ethyl chloroformate, ethyl bromoformate, isobutyl chloroformate or the like can be exemplified. Generally, said alkylhalocarboxylic acid is used at least an equimolar quantity, preferably about 1 to 2 times the molar quantity to one molar quantity of a carbostyril derivative of the general formula (2). The amount of an amine of the general formula (3) is used generally at least an equimolar quantity, preferably about 1 to 2 times the molar quantity to one molar quantity of a carbostyril derivative of the general formula (2).

The above-mentioned activated ester method (b) is carried out, for example in the case of using an N-hydroxysucciniimide ester, the reaction is carried out in a suitable inert solvent which does not give any adverse effects to the reaction. As to the solvent, specifically, a halogenated hydrocarbon such as methylene chloride, chloroform, dichloroethane or the like; an aromatic hydrocarbon such as benzene, toluene, xylene or the like; an ether such as diethyl ether, tetrahydrofuran, dimethoxyethane or the like, an ester such as methyl acetate, ethyl acetate or the like; an aprotic polar solvent such as N,N-dimethylformamide, dimethyl sulfoxide, hexamethylphosphoric triamide or the like can be exemplified. The reaction is carried out at about $0°$ to $150°$ C., preferably at about $10°$ to $100°$ C., and is completed in about 5 to 30 hours. The amount of an amine of the general formula (3) is used generally at least an equimolar quantity, preferably an equimolar quantity to 2 times the molar quantity to one molar quantity of the N-hydroxysuccinimide ester.

The above-mentioned carboxylic acid halide method (d-3), thus reacting a carboxylic acid halide with an amine is carried out in a suitable solvent in the presence of a dehydrohalogenating agent. As to the dehydrohalogenating agent, a usual basic compound may be used. As to the basic compound, those are known widely can be used, for example, basic compounds used in Schotten-Baumann reaction, and also sodium hydroxide, potassium hydroxide, sodium hydride, potassium hydride, silver carbonate, an alcoholate such as sodium methylate sodium ethylate or the like may be exemplified. Furthermore, an excess amount of an amine of the general formula (3) can also be used as the dehydrohalogenating agent. As to the solvent, in addition to those used in the above-mentioned mixed acid anhydride method (a), the following solvents for example alcohols such as methanol, ethanol, propanol, butanol, 3-methoxy-1-butanol, ethyl cellosolve, methyl cellosolve and the like; pyridine, acetone, acetonitrile or the like, or a mixed solvent containing two or more of the above-mentioned solvents can also be used.

Ratio of the amounts of an amine of the general formula (3) and the carboxylic acid halide is not specifically restricted and it can be selected from a wide range, and generally at least an equimolar quantity, preferably an equimolar to 2 times the molar quantity of the latter may be used to the former. The reaction is generally carried out at about $-30°$ to $180°$ C., preferably at about $0°$ to $150°$ C., and the reaction is generally completed in 5 minutes to 30 hours. In the above-mentioned reaction, the carboxylic acid halide is prepared by reacting a carbostyril derivative of the general formula (2) with a halogenating agent in the absence or presence of a solvent. As to the solvent, any solvent which does not give any adverse effect to the reaction can be used, for example an aromatic hydrocarbon such as benzene, toluene, xylene or the like; a halogenated hydrocarbon such as chloroform, methylene chloride, carbon tetrachloride or the like; an ether such as dioxane, tetrahydrofuran, diethyl ether or the like; dimethylformamide, dimethyl sulfoxide or the like can be exemplified. As to the halogenating agent, a usual halogenating agent which can be able to convert the hydroxy group into halogen atom may be used, for example thionyl chloride, phosphorus oxychloride, phosphorus oxybromide, phosphorus pentachloride, phosphorus pentabromide or the like may be exemplified.

Ratio of the amounts of a carbostyril derivative of the general formula (2) and the halogenating agent is not specifically restricted, and it can be selected from a wide range, and in the case of carrying out the reaction in the absence of a solvent, generally a large excess amount of the latter is used to the former. In the case of carrying out the reaction in the presence of a solvent, at least an equimolar quantity, preferably 2 to 4 times the molar quantity of the latter is used to the former. The reaction temperature and reaction time are not specifically restricted, and generally the reaction is carried out at room temperature to $100°$ C., preferably at about $50°$ to $80°$ C., for about 30 minutes to 6 hours.

In carrying out of the above-mentioned method (d-4) in which a carbostyril derivative of the general formula (2) is activated with a phosphorus compound such as triphenylphosphine or diethylchlorophosphate, and then said activated carbostyril derivative is reacted with an amine of the general formula (3) in a suitable solvent.

As to the solvent, any solvent which does not give any adverse effect to the reaction can be used, and specifically a halogenated hydrocarbon such as methylene chloride, chloroform, dichloroethane or the like; an aromatic hydrocarbon such as benzene, toluene, xylene or the like, an ether such as diethyl ether, tetrahydrofuran, diethoxyethane or the like, an ester such as methyl acetate, ethyl acetate or the like; an aprotic polar solvent such as N,N-dimethylformamide, dimethyl sulfoxide, hexamethylphosphoric triamide or the like can be exemplified. In the above-mentioned reaction, the amine of the general formula (3) per se works as the basic compound, the reaction can be proceeded smoothly when the amine is used in a large excess quantity over the stoichiometric amount. If necessary, other basic compound, for example an organic base such as triethylamine, trimethylamine, pyridine, dimethylaniline, N-methylmorpholine, DBN, DBU, DABCO or the like; an inorganic base such as potassium carbonate, sodium carbonate, potassium bicarbonate, sodium bicarbonate or the like can be used. The reaction is carried out at about 0° to 150° C., preferably at about 0° to 100° C. for about 1 to 30 hours. Ratio of the amounts of the phosphorus compound and the amine of the general formula (3) to the amount of the carbostyril derivative of the general formula (2) is generally at least an equimolar quantity, preferably about 1 to 3 times the molar quantity respectively.

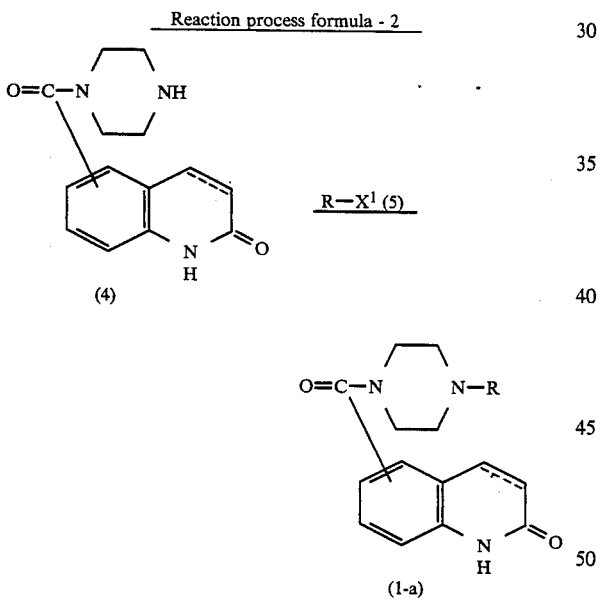

[wherein R and the carbon-carbon bond between 3- and 4-positions in the carbostyril skeleton are the same as defined above; $X^1$ is a halogen atom, a lower alkanesulfonyloxy group, an arysulfonyloxy group or an aralkylsulfonyloxy group.

The compound represented by the general formula (1-a) is prepared by reacting a compound of the general formula (4) with a compound represented by the general formula (5). This reaction can be carried out by procedures and conditions similar to those employed in the abovementioned reaction of a carboxylic acid halide with an amine of the general formula (3). Said reaction can be carried out advantageously by adding copper compound such as copper iodide or copper powder.

In the definition of $X^1$ in the general formula (5), the specific examples of the halogen atom are chlorine, fluorine, bromine and iodine atoms; the specific examples of the lower alkanesulfonyloxy group are methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy groups and the like; the specific examples of the arylsulfonyloxy group are substituted- or unsubstituted-arylsulfonyloxy groups such as phenylsulfonyloxy, 4-methylphenylsulfonyloxy, 2-methoxyphenylsulfonyloxy, 4-nitrophenylsulfonyloxy, 4-methoxyphenylsulfonyloxy, 3-chlorophenylsulfonyloxy, α-naphthylsulfonyloxy groups and the like; furthermore, the specific examples of the aralkylsulfonyloxy group are substituted- or unsubstituted-aralkylsulfonyloxy groups such as bonzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy groups and the like.

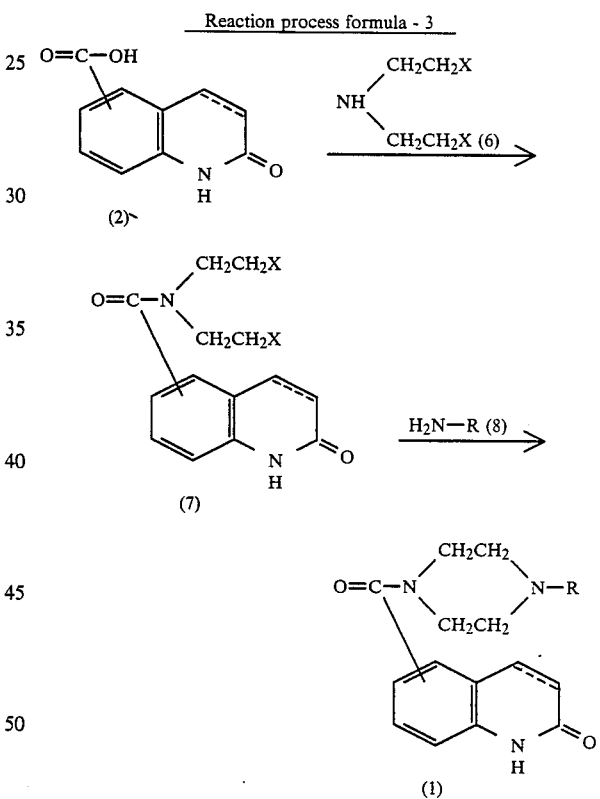

[wherein R and the carbon-carbon bond between 3- and 4-positions in the carbostyril skeleton are the same as defined above; X is a hydroxy group together with the definition same as defined in the above-mentioned $X^1$].

A carbostyril derivative represented by the general formula (1) can be prepared by reacting a known compound of the general formula (2) with a compound of the general formula (6) to prepare a known compound of the general formula (7), then reacting said compound of the general formula (7) with a compound of the general formula (8). The first step in the above-mentioned reaction process is carried out by procedures and conditions similar to those employed in the reaction of a compound of the general formula (2) with a compound of the general formula (3) shown in the reaction process formula 1.

The second step followed after the first step in the above-mentioned reaction process is carried out by the procedures as mentioned below depend on the type of the substituent defined in the symbol X in the general formula (7). Thus, in the case of using a compound of the general formula (7) wherein X is a halogen atom, a lower alkanesulfonyloxy group, an arylsulfonyloxy group or an aralkylsulfonyloxy group, the reaction of a compound of the general formula (7) with a compound of the general formula (8) is generally carried out, in a suitable inert solvent in the presence of or absence of a basic condensing agent. As to the inert solvent, aromatic hydrocarbons such as benzene, toluene, xylene and the like; lower alcohols such as methanol, ethanol, isopropanol, butanol and the like; acetic acid, ethyl acetate, dimethyl sulfoxide, dimethylformamide, hexamethylphosphoric triamide and the like can be exemplified. As to the basic condensing agent, alkali or alkaline earth metal carbonates such as sodium carbonate, potassium carbonate, sodium biarbonate, potassium bicarbonate and the like; metal hydroxides such as sodium hydroxide, potassium hydroxide and the like; metal alcoholates such as sodium methylate, sodium ethylate and the like; organic basic compounds such as pyridine, triethylamine and the like can be exemplified.

The ratio of the amount of a compound of the general formula (7) to the amount of a compound of the general formula (8) is not specifically restricted, and it can be selected from a wide range, generally at least an equimolar quantity, preferably an equimolar to 5 times the molar quantity of the latter may be used to the former. The reaction is generally carried out at about 40°-120° C., preferably at about 50°-100° C., and is completed in about 5 to 30 hours.

In the case of using a compound of the general formula (7) wherein X is a hydroxy group, the reaction of a compound of the general formula (7) with a compound of the general formula (8) is carried out in the presence of a dehydro-condensing agent in the absence or presence of a suitable solvent. As to the dehydro-condensing agent, condensed phosphoric acids such as polyphosphoric acid; phosphoric acids such as orthophosphoric acid, pyrophosphoric acid, metaphosphoric acid and the like; phosphorous acids such as orthophosphorous acid and the like; anhydrous phosphoric acid such as phosphorus pentoxide; mineral acids such as hydrochloric acid, sulfuric acid, boric acid and the like; metal phosphates such as sodium phosphate, boron phosphate, ferric phosphate, aluminium phosphate and the like; activated alumina, sodium bisulphite, Raney nickel and the like can be exemplified. As to the inert solvent, solvents having high boiling point such as dimethylformamide, tetrahydronaphthalene and the like can be exemplified.

The ratio of the amount of a compound of the general formula (7) to the amount of a compound of the general formula (8) is not specifically restricted, and can be selected from a wide range, and generally, 0.8 molar quantity or more, preferably, 0.8 to 2 times the molar quantity of the latter may be used to the former. The ratio of the amount of the dehydro-condensing agent is not specifically restricted and it can be selected from a wide range, and generally a catalytic amount or more, preferably 0.5–5 times the molar quantity may be used to the compound of the general formula (7). In order to prevent from adverse effects of the oxidation reaction, the above-mentioned reaction can be carried out in an inert gas atmosphere for example carbon dioxide gas or nitrogen gas stream. The reaction is carried out generally under a normal atmospheric pressure, at about 100°-350° C., preferably at 125°-255° C., for about 3 to 10 hours.

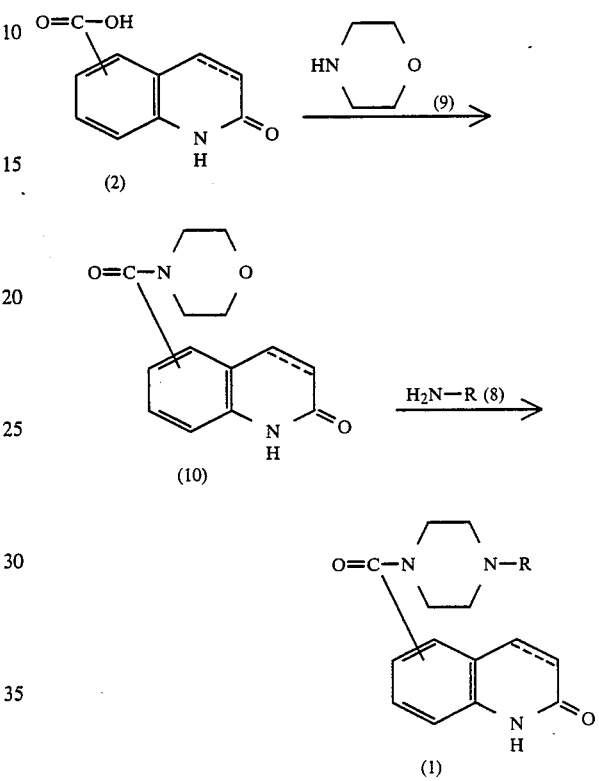

[wherein R and the carbon-carbon bond between 3- and 4-positions in the carbostyril skeleton are the same as defined above].

A carbostyril derivative represented by the general formula (1) can also be prepared by reacting a compound of the general formula (2) with morpholine (9) to obtain a known morpholine derivative of the general formula (10), then reacting said morpholine derivative of the general formula (10) with a compound of the general formula (8).

The reaction of a compound of the general formula (2) with morpholine (9) can be carried out by procedures and conditions similar to those employed in the reaction of a compound of the general formula (2) with a compound of the general formula (3). Furthermore, the reaction of the thus obtained compound of the general formula (10) with a compound of the general formula (8) is carried out in the absence or presence of a suitable solvent, in the presence of an acid. As to the solvent, a solvent having high boiling point such as tetrahydronaphthalene, dimethylformamide, dimethyl sulfoxide, hexamethylphosphoric triamide or the like can be used. As to the acid, hydrochloric acid, sulfuric acid, hydrobromic acid or the like can be used.

The ratio of the amount of a compound of the general formula (10) to the amount of a compound of the general formula (8) is not specifically restricted and it can be selected from a wide range, generally at least an equimolar quantity, preferably an equimolar to 2 times the molar quantity of the latter may be used to the former. The reaction is generally carried out at about 50°–250° C., preferably at about 150°–200° C., and is completed in about 1 to 24 hours.

Among compounds represented by the general formula (1), a compound of the general formula (1-a) is prepared by the following reaction process formula 5.

Reaction process formula - 5

O=C–N⟨  ⟩N–A–C(=O)–R²
[carbostyril]
(1-b)

→ Hydrogenation →

O=C–N⟨  ⟩N–A–CH(OH)–R²
[carbostyril]
(1-a)

[wherein A, R² and the carbon-carbon bond between 3- and 4-positions in the carbostyril skeleton are the same as defined above].

The hydrogenation of a compound of the general formula (11) can be carried out by applying various methods of reduction, and for example a method by using a hydrogenation reducing agent is preferably applied. As to the hydrogenation reducing agent, for example lithium aluminium hydride, sodium borohydride, diborane and the like can be exemplified. The amount of said reducing agent is at least an equimolar quantity, preferably within the range of an equimolar to 10 times the molar quantity. The reduction is generally carried out in a suitable solvent, for example water, a lower alcohol such as methanol, ethanol, isopropanol or the like; an ether such as tetrahydrofuran, diethyl ether, diethylen glycol dimethyl ether or the like; a polar solvent such as dimethylformamide, acetic acid or the like; or a mixed solvent thereof, and generally at about −60° to 50° C., preferably at about 30° C. to room temperature, for about 10 minutes to 3 hours. In the case of using lithium aluminium hydride or diborane as the reducing agent, the reduction may be carried out in an anhydrous solvent such as diethyl ether, tetrahydrofuran, diethylene glycol dimethyl ether or the like.

A compound represented by the general formula (1-b) can be prepared by a method of the following reaction process formula 6.

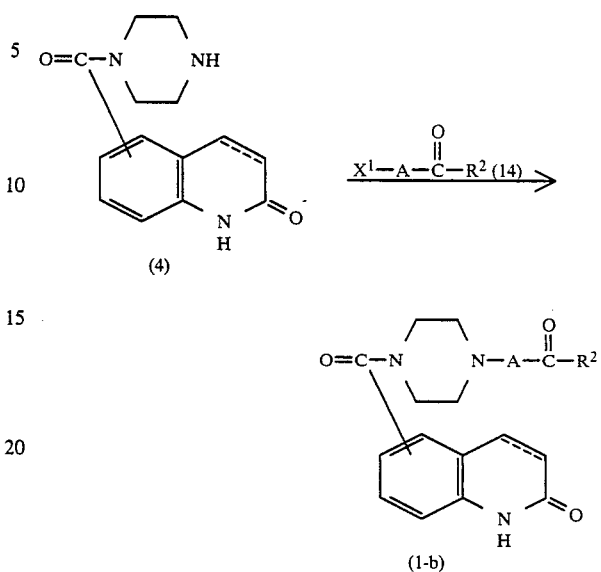

Reaction process formula - 6

[wherein A, R², X¹ and the carbon-carbon bond between 3- and 4-positions in the carbostyril skeleton are the same as defined above].

The reaction of a compound of the general formula (4) with a compound of the general formula (14) is carried out in the presence of a dehydrohalogenating agent in a suitable solvent. As to the dehydrohalogenating agent, common basic compound can be used, for example an organic base such as triethylamine, trimethylamine, pyridine, dimethylaniline, N-methylmorpholine, 4-dimethylaminopyridine, 1,5-diazabicyclo[4,3,0-]nonene-5 (DBN), 1,8-diazabicyclo[5,4,0]undecene-7 (DBU), 1,4-diazabicyclo[2,2,2]octane (DABCO) or the like, an inorganic base such as sodium hydroxide, potassium hydroxide, silver carbonate, an alcoholate such as sodium methylate, sodium ethylate, potassium carbonate, sodium carbonate, potassium bicarbonate, sodium bicarbonate or the like. As to the solvent, a halogenated hydrocarbon such as methylene chloride, chloroform, dichloromethane or the like; an aromatic hydrocarbon such as benzene, toluene, xylene or the like; an ether such as diethyl ether, tetrahydrofuran, dimethoxyethane or the like; an ester such as methyl acetate, ethyl acetate or the like; an aprotic polar solvent such as N,N-dimethylformamide, dimethyl sulfoxide, hexamethylphosphoric triamide or the like; an alcohol such as methanol, ethanol, propanol, butanol, 3-methoxy-1-butanol, ethyl cellosolve, methyl cellosolve or the like; pyridine, acetone, acetonitrile or the like, or a mixed solvent thereof.

The ratio of the amount of a compound of the general formula (4) to the amount of a compound of the general formula (14) is not specifically restricted, and may be selected from a wide range, generally at least an equimolar quantity, preferably an equimolar to 2 times the molar quantity of the latter may be used to the former. The reaction is generally carried out at about −30° to 180° C., preferably at about 0° to 150° C., and is completed in 5 minutes to 30 hours.

Reaction process formula - 7

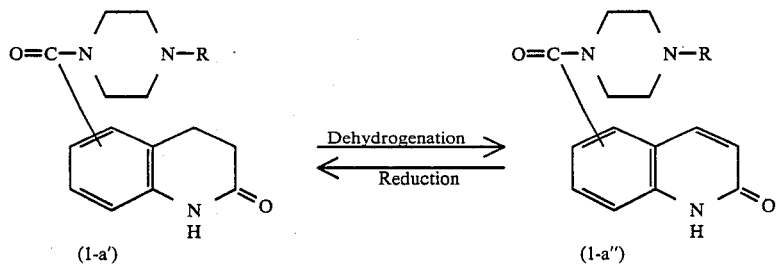

[wherein R is the same as defined above].

The reduction of a compound of the general formula (1-a") is carried out under conditions similar to those employed in usual catalytic reduction method. As to the catalyst used, a metal catalyst such as palladium, palladium-carbon, platinum, Raney nickel or the like can be exemplified. The catalyst may be used in a usual catalytic amount. As to the solvent used, water, methanol, ethanol, isopropanol, dioxane, tetrahydrofuran, hexane, cyclohexan, ethyl acetate or a mixed solvent thereof can be exemplified. The reduction can be carried out either a normal atmospheric pressure or under a pressure, and generally, a normal atmospheric pressure to 20 kg/cm², preferably a normal pressure to 10 kg/cm². The reduction is generally carried out at about 0° to 150° C., preferably at about room temperature to 100° C.

The dehydrogenation of a compound of the general formula (1-a') is carried out in a suitable solvent with an oxidizing agent. As to the oxidizing agent, a benzoquinone such as 2,3-dichloro-5,6-dicyanobenzoquinone, chloranil (2,3,5,6-tetrachlorobenzoquinone) or the like; a halogenating agent such as N-bromosuccinimide, N-chlorosuccinimide or bromine; a dehydrogenating catalyst such as selenium dioxide, palladium-carbon, palladium black, palladium oxide, Raney nickel or the like can be exemplified. The amount of oxidizing agent is not specifically restricted and can be selected from a wide range, and generally in the case of using halogenating agent, generally 1-5 times the molar quantity, preferably 1-2 times the molar quantity of the halogenating agent may be used to the compound of the general formula (1-a'). Further, in the case of using a dehydrogenating catalyst, generally an excess amount thereof may be used. As to the solvent, an ether such as dioxane, tetrahydrofuran, methoxyethanol, dimethoxyethanol or the like; an aromatic hydrocarbon such as benzene, toluene, xylene, cumene or the like; a halogenated hydrocarbon such as dichloromethane, dichloroethane, chloroform, carbon tetrachloride, or the like; an alcohol such as butanol, amyl alcohol, hexanol, or the like; a protic polar solvent such as acetic acid; an aprotic polar solvent such as dimethylformamide, dimethyl sulfoxide, hexamethylphosphoric triamide or the like can be exemplified. The reaction is generally carried out at room temperature to 300° C., preferably at room temperature to 200° C., and is completed in about 1 to 40 hours.

Among carbostyril derivatives represented by the general formula (1), those having double bond between 3- and 4-positions in the carbostyril skeleton can be taken lactam-lactim tautomerism as shown in the following reaction process formula 8.

Reaction process formula - 8

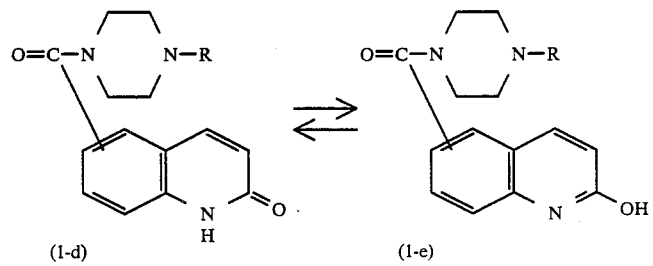

[wherein R is the same as defined above].

Reaction process formula - 9

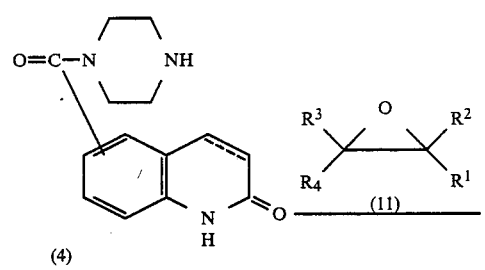

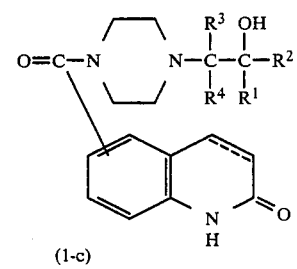

[wherein R¹, R², and the carbon-carbon bond between 3- and 4-positions in the carbostyril skeleton are the same as defined above; and R³ and R⁴ are the same or different from each other and are each a hydrogen atom or a lower alkyl group].

The reaction of a compound of the general formula (4) with a compound of the general formula (11) can be carried out in the presence or absence of a suitable solvent in the presence or absence of a basic compound. The reaction is generally carried out at about room temperature to 200° C., preferably at about 60° to 120° C., and is completed in about 1–24 hours. As to the solvent used in this reaction, an ether such as dioxane, tetrahydrofuran, ethylene glycol dimethyl ether, diethyl ether or the like; an aromatic hydrocarbon such as benzene, toluene, xylene or the like; a lower alcohol such as methanol, ethanol, isopropanol or the like; a polar solvent such as N-methylpyrrolidone, dimethylformamide, dimethyl sulfoxide, hexamethylphosphoric triamide or the like can be exemplified. As to the basic compound, an inorganic base such as potassium carbonate, sodium carbonate, sodium hydroxide, sodium bicarbonate, sodium amide or the like can be exemplified, and an organic base such as triethylamine, tripropylamine, pyridine, quinoline or the like can be exemplified.

The amount of a compound of the general formula (11) to the amount of a compound of the general formula (4) may be at least an equimolar quantity, preferably an equimolar to 5 times the molar quantity of the former to the latter.

A compound of the general formula (11) can be prepared by the following reaction process formula 10.

Reaction process formula - 10

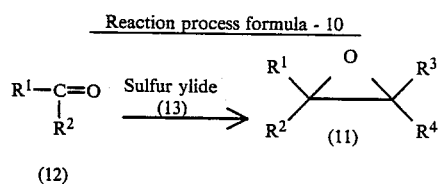

(12)

[wherein $R^1$, $R^2$, $R^3$ and $R^4$ are the same as defined above.]

The reaction of a compound of the general formula (12) with sulfur ylide compound of the general formula (13) can be carried out in a suitable solvent. As to the solvent used in this reaction, an ether such as terahydrofuran or the like; a polar solvent such as dimethylformamide, dimethyl sulfoxide or the like can be exemplified. The reaction is carried out generally at about $-50°$ to 70° C., preferably at $-30°$ to 50° C., and is completed in about 10 minutes to 5 hours. The amount of sulfur ylide compound of the general formula (13) to the amount of a compound of the general formula (12) may be at least an equimolar quantity, preferably an equimolar to 2 times the molar quantity of the former to the latter. As to the sulfur ylide compound of the general formula (13), a compound of the formula

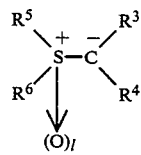

(wherein $R^3$ and $R^4$ are the same as defined above; $R^5$ and $R^6$ are the same or different from each other, and are each a lower alkyl group, a phenyl group, a lower alkylamino group, a phenyl-lower alkyl group, a lower alkenyl group or a lower alkoxy group; l is an integer of 0 or 1) can be exemplified.

Among compounds represented by the general formula (1), those having a phenyl-lower alkenyl group which has a lower alkylthio groups as the substituents on the phenyl ring, or having a phenyl group which may have 1 to 3 lower alkylthio groups as the substituents as the symbol of R or $R^2$, such compounds can be converted into those having a phenyl-lower alkenyl group which has lower alkylsulfinyl group as the substituents on the phenyl ring, or having a phenyl group which has 1 to 3 lower alkylsulfinyl groups, by oxidizing in a suitable solvent in the presence of an oxidizing agent. As to the solvent used in this reaction, water, an organic acid such as formic acid, acetic acid, trifluoroacetic acid or the like; an alcohol such as methanol, ethanol or the like; a halogenated hydrocarbon such as chloroform, dichloromethan or the like; or a mixed solvent of thereof can be exemplified. As to the oxidizing agent, any oxidizing agent which can be able to oxidize the sulfide group to sulfoxide group can be used, for example, per acid such as performic acid, peracetic acid, pertrifluoroacetic acid, perbenzoic acid, m-chloroperbenzoic acid, o-carbonylperbenzoic acid or the like; hydrogen peroxide; dichromic acid, dichromate such as sodium dichomate, potassium dichromate; permanganic acid, permanganate such as sodium permanganate, potassium permanganate or the like can be exemplified. The amount of the oxidizing agent may be at least an equimolar quantity, perferably an equimolar to 4 times the molar quantity thereof to the compound to be oxidized (a compound having alkylthio group). The oxidation reaction is generally carried out at $-20°$ to 40° C., preferably at $-20°$ to room temperature, and is completed in 0.5 to 50 hours.

Among carbostyril derivative represented by the general formula (1) according to the present invention, those having basic group can easily be converted into an acid-addition salt thereof by reacting with a pharmaceutically acceptable acid. As to the acid, inorganic acids such as hydrochloric acid, sulfuric acid, phosphoric acid and hydrobromic acid and the like; organic acids such as oxalic acid, maleic acid, fumaric acid, malic acid, tartaric acid, citric acid, benzoic acid and the like can be exemplified.

The objective compounds prepared by the procedures in the respective reaction process formulas as mentioned above can easily be isolated and purified by conventional separation means, such as a solvent extraction method, a dilution method, a recrystallization method, a column chromatography method, a preparative thin-layer chromatography method or the like.

Furthermore, carbostyril derivatives represented by the general formula (1) according to the present invention inevitably including their optical isomers.

A carbostyril derivative represented by the general formula (1) according to the present invention and salt thereof can generally be used in the form of a pharmaceutical composition. Such pharmaceutical composition can be prepared by using diluents or excipients such as fillers, diluents, binders, wetting agents, disintegrators, surface active agents, lubricants, etc. The pharmaceutical composition can be selected from any desired form, including tablets, pills, powders, liquors, suspensions, emulsions, granules, capsules, suppositories and injections (e.g., solutions, suspensions, etc.).

For the purpose of shaping in the form of tablets, carriers which are known in this field can be used, for example, excipients such as lactose, sucrose, sodium chloride, glucose, urea, starch, calcium carbonate, kaolin, crystalline cellulose, silicic acid, etc; binding agents such as water, ethanol, propanol, simple syrup, a solution of glucose, a solution of gelatin, carboxylmethyl cellulose, shelac, methylcellulose, calcium phosphate, polyvinylpyrrolidone, etc; disintegrators such as dried starch, sodium alginate, agar-agar powder, laminalia powder, sodium bicarbonate, calcium carbonate, esters of polyoxyethylene sorbitan fatty acids, sodium laurylsulfate, monoglycerides of stearic acid, starch, lactose, etc; disintegration inhibiting agents such as sucrose, stearin, coconut butter, hydrogenated oil, etc.; absorption accelerators such as a quaternary ammonium base, sodium laurylsulfate, etc.; wetting agents such as glycerin, starch, etc.; adsorbing agents such as starch, lactose, kaolin, bentonite, colloidal silicic acid, etc.; lubricants such as purified talc, stearic acid salts, boric acid power, polyethylene glycol, etc. In the case of preparing tablets, they can be further coated with an usual coating material to make them as in the form of sugar coated tablets, gelatin film coated tablets, tablets coated with enteric coatings, tablets coated with films or double-layered tablets and multi-layered tablets.

For the purpose of shaping in the form of pills, carriers which are known and used widely in this field can also be used, such as excipients for example glucose, lactose, starch, coconut butter, hydrogenated vegetable oil, kaolin, talc, etc.; binding agents such as gum arabic powder, tragacanth gum powder, gelatin, ethanol, etc.; disintegrators such as laminaria, agar-agar, etc.

For the purpose of shaping in the form of suppositories, carriers which are known and used widely in this field can be used, for example polyethylene glycols, coconut butter, higher alcohols, esters of higher alcohols, gelatin, semi-synthesized glycerides, etc.

For the purpose of shaping in the form of injection preparations, solutions and suspensions are sterilized and are preferably isotonic to the blood. In the case of making injection preparations in the form of solutions, emulsions and suspensions, diluents which are commonly used in this field can also be used, for example water, ethanol, propylene glycol, ethoxylated isostearyl alcohol, polyoxylated isostearyl alcohol, polyoxyethylene sorbitan fatty acid esters, etc. can be exemplified. In these cases, adequate amounts of sodium chloride, glucose or glycerin can be added to the injection preparations so as to make them isotonic to the blood. Furthermore, usual dissolving agents, buffer solutions, analgesic agents can be added, as well as coloring agents, perfumes, preservatives, seasoning agents, sweetening agents and other medicaments can be added into the desired pharmaceutical preparations, if necessary.

The amount of carbostyril derivative represented by the general formula (1) to be contained in the cardiotonic composition according to the present invention is not specifically restricted and can easily be selected from a wide range, and generally 1 to 70% by weight, preferably 1 to 30% by weight of carbostyril derivative of the general formula (1) may be contained in the whole composition.

Mode of administrations of the cardiotonic composition according to the present invention is not specifically restricted, and can be administered in various forms depending on the purpose of the administration, forms of the preparations, the age of the patient, the distinction of sex, the conditions of the symptoms and other factors. For example, tablets, pills, solutions, suspensions, emulsions, granules and capsules are administered orally, and injection preparations are administered intraveneously singly or are mixed with injection transfusions such as glucose solutions and amino acids solutions; if necessary the injection preparations are administered singly intramuscularly, intracutaneously, subcutaneously or intraperitoneally, and suppositories are administered into rectum.

The administration dosage of a cardiotonic composition according to the present invention is suitably selected depend on the usage, the age of the patient, the distinction of sex, the condition of the symptoms and other factors, generally 0.01 to 10 mg/kg of the body weight per day of carbostyril derivative represented by the general formula (1) as the active ingredient may be administered, and 0.1 to 200 mg of the active ingredient may be contained in the administration unit form.

The present invention will be illustrated more specifically by way of showing the following examples, in which preparation of the compounds to be used as the starting materials will be shown in Reference Examples, preparations of the objective carbostyril derivatives will be shown in Examples, and cardiotonic compositions will be shown in Examples of Pharmaceutical Preparations, however the present invention are not restricted only to these examples.

Reference Example 1

1.7 Grams of 2-(4-methoxybenzoyl)ethyl bromide, 1.4 g of 6-(1-piperazinylcarbonyl)-3,4-dihydrocarbostyril monohydrochloride and 1.4 g of potassium carbonate were suspended in 40 ml of dimethylformamide, then the suspension thus prepared was stirred at room temperature for 2 hours. After the reaction was finished, the reaction mixture was poured in 150 ml of water, and extracted with ethyl acetate. The extract was washed with water, dried then the solvent was removed by evaporation. The residue thus obtained was dissolved in methanol, and the pH of the methanol solution was adjusted to about pH=1 with hydrochloric acid. The solvent was removed by evaporation, then the residue was recrystallized from ethanol-water to obtain 3 g of 6-{4-[(2-methoxybenzoyl)ethyl]-1-piperazinylcarbonyl}-3,4-dihydrocarbostyril monohydrochloride monohydrate. Melting point: 204°–205° C. (dec.). Colorless rhombohedral crystals.

Reference Examples 2–4

By a procedure similar to that described in Reference Example 1, there were prepared compounds as follows:

| Reference Example No. | Compound |
| --- | --- |
| 2 | 6-{4-[2-(4-Methylthiobenzoyl)ethyl]-1-piperazinyl}-3,4-dihydrocarbostyril Colorless prism-like crystals (recrystallized from dichloromethane-methanol) Melting point: 184–186° C. |
| 3 | 6-{4-[3-(4-Methylthiobenzoyl)propyl]-1-piperazinyl}-3,4-dihydrocarbostyril hydrochloride ½-hydrate Colorless powdery crystals (recrystallized from ethanol-water) Melting point: 257–259° C. (ded.) |
| 4 | 6-{4-[3-(4-Fluorobenzoyl)propyl]-1-piperazinyl}-3,4-dihydrocarbostyril hydrochloride ⅔-hydrate Colorless powdery crystals (recrystallized from ethanol-water) |

-continued

| Reference Example No. | Compound |
|---|---|
| | Melting point: 244–245° C. (dec.) |

Reference Example 5

Under nitrogen gas stream condition, 40 ml of dimethyl sulfoxide was added to 3.3 g of sodium hydride (60% in oil), then this mixture was heated at 60° C. for 1 hour under stirring. The reaction mixture was cooled to room temperature, then was added 40 ml of tetrahydrofuran thereto. To this reaction mixture was added dropwise 60 ml of dimethyl sulfoxide solution containing 16.9 g of trimethylsulfonium iodide within 3 minutes. Next, 4.9 ml of acetophenone was added immediately to this reaction mixture, and the whole mixture was stirred at 0° C. for 6 minutes, then at room temperature for 1 hour. The reaction mixture was poured into 500 ml of ice-water, and extracted with diethyl ether. The diethyl ether extract was washed with water, dried with anhydrous sodium sulfate, then the solvent was removed under reduced pressure in the presence of a slight amount of potassium carbonate to yield 3.8 g of 2-phenyl-2-methylepoxide. Colorless oily substance. Boiling point: 83°–86° C. at 20 mm Hg.

EXAMPLE 1

2.8 Grams of 6-{4-[2-(4-methoxybenzoyl)ethyl]-1-piperazinylcarbonyl}-3,4-dihydrocarbostyril was suspended in 150 ml of methanol-dimethylformamide [1:1(v/v)] then 0.26 g of sodium borohydride was added thereto at room temperature and stirred for 1 hour. The excess sodium borohydride was decomposed by adding 2M-hydrochloric acid to the reaction mixture, and the solvent was removed by evaporation. The residue was treated with a mixture of water-ethyl acetate, and the organic layer was washed with water, dried then the solvent was removed by evaporation. The residue thus obtained was converted into hydrochloride by adding ethanol-concentrated hydrochloric acid, and the thus obtained hydrochloride was recrystallized from ethanol-water to obtain 0.9 g of 6-{4-[3-(4-methoxyphenyl)-3-hydroxypropyl]-1-piperazinylcarbonyl}-3,4-dihydrocarbostyril monohydrochloride. Melting point: 219°–224° C. (dec.). Colorless powdery substance.

EXAMPLES 2-21

By method similar to that described in Example 1, and by using a suitable starting material, there were prepared compounds of Examples 2-21 as shown in Table 1.

TABLE 1

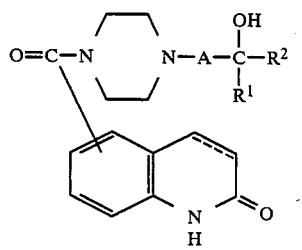

| Example No. | A | R¹ | R² | Substituted position of the side-chain | Carbon-carbon bond between 3- and 4- positions | Melting point (°C.) (Recrystallization Solvent) | Crystal form | Salt |
|---|---|---|---|---|---|---|---|---|
| 2 | —(CH₂)₂— | H | phenyl | 6 | Single | 236–238 (Ethanol-water) | Colorless powdery substance | HCl |
| 3 | —(CH₂)₃ | H | phenyl | 6 | Single | 230–232 (Ethanol-water) | Colorless powdery substance | HCl |
| 4 | —(CH₂)₂— | H | 4-CH₃-phenyl | 6 | Single | 235–237 (Ethanol-water) | Colorless powdery substance | HCl |
| 5 | —CH₂— | H | 3-Cl-phenyl | 6 | Single | 230–239 (dec.) (Isopropanol-water) | Colorless powdery substance | HCl |

TABLE 1-continued

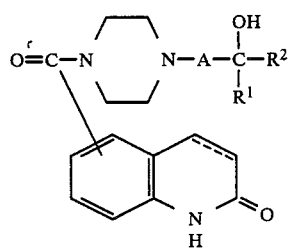

| Example No. | A | $R^1$ | $R^2$ | Substituted position of the side-chain | Carbon-carbon bond between 3- and 4- positions | Melting point (°C.) (Recrystallization Solvent) | Crystal form | Salt |
|---|---|---|---|---|---|---|---|---|
| 6 | $-(CH_2)_2-$ | H | ⏤⟨⟩⏤NHCOCH₃ | 6 | Single bond | 190–194 (dec.) (Ethanol-water) | Colorless powdery substance | HCl. ½-H₂O |
| 7 | $-CH_2-$ | H | ⏤⟨⟩⏤OH | 6 | Single bond | 212–214 (dec.) (Ethanol-water) | Colorless powdery substance | — |
| 8 | $-CH_2-$ | H | ⏤⟨⟩ | 6 | Single bond | 214–233 (dec.) (Ethanol-water) | Colorless powdery substance | HCl. ½-H₂O |
| 9 | $-(CH_2)_2-$ | H | ⏤⟨⟩⏤CH₃ | 6 | Double bond | 236–243 (dec.) (Ethanol-water) | Colorless powdery substance | HCl |
| 10 | $-(CH_2)_3-$ | H | ⏤⟨⟩⏤Cl | 6 | Single bond | 223–226 (Ethanol-water) | Colorless powdery substance | HCl |
| 11 | $-(CH_2)_2-$ | H | ⏤⟨⟩⏤SCH₃ | 6 | Single bond | 245–247 (dec.) (Ethanol-water) | Colorless prism-like crystals | HCl |
| 12 | $-(CH_2)_2-$ | H | ⏤⟨⟩⏤S(O)CH₃ | 6 | Single bond | 230–240 (dec.) (Ethanol-water) | Colorless prism-like crystals | HCl |
| 13 | $-CH_2-$ | H | ⏤⟨⟩⏤F | 6 | Single bond | 254–256 (dec.) (ethanol-water) | Colorless powdery substance | HCl. ½-H₂O |
| 14 | $-(CH_2)_3-$ | H | ⏤⟨⟩⏤SCH₃ | 6 | Single bond | 254–256 (dec.) (Ethanol-water) | Colorless powdery substance | HCl. ½-H₂O |
| 15 | $-(CH_2)_3-$ | H | ⏤⟨⟩⏤S(O)CH₃ | 6 | Single bond | 204–205 (dec.) (Ethanol-water) | Colorless powdery substance | HCl.H₂O |

TABLE 1-continued

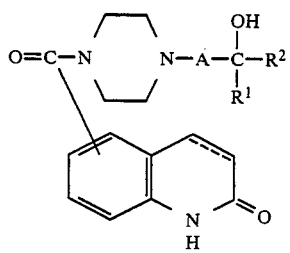

| Example No. | A | R¹ | R² | Substituted position of the side-chain | Carbon-carbon bond between 3- and 4- positions | Melting point (°C.) (Recrystallization Solvent) | Crystal form | Salt |
| --- | --- | --- | --- | --- | --- | --- | --- | --- |
| 16 | —(CH₂)₃— | H | —C₆H₄—F (4-F) | 6 | Single bond | 247–248 (dec.) (Ethanol-water) | Colorless powdery substance | HCl.H₂O |
| 17 | —(CH₂)₂— | H | —C₆H₄—F (4-F) | 6 | Single bond | 229–230 (dec.) (Ethanol-water) | Colorless powdery substance | HCl |
| 18 | —CH₂— | H | —C₆H₄—Cl (4-Cl) | 6 | Single bond | 154–157 (dec.) (Ethanol) | Colorless powdery substance | HCl |
| 19 | —(CH₂)₂— | H | —C₆H₅ | 8 | Double bond | 169–172 (Ethanol) | Colorless powdery substance | — |
| 20 | —(CH₂)₂— | H | —C₆H₅ | 7 | Single bond | 177–178 (Ethanol) | Colorless powdery substance | — |
| 21 | —(CH₂)₂— | H | —C₆H₅ | 5 | Double bond | 163–166 (Ethanol) | Colorless powdery substance | — |

EXAMPLE 22

4.2 Grams of 6-(1-piperazinylcarbonyl)-3,4-dihydrocarbostyril and 30 ml of N-methylpyrrolidone solution containing 2.0 g of 2-phenyl-2-methylepoxide were mixed together and this mixture was heated at 100°–110° C. for 11 hours with stirring. After the reaction was completed, the solvent was removed by evaporation under reduced pressure. The residue thus obtained was purified by means of a silica gel column chromatography (eluent: methanol:dichloromethane=1:25). Recrystallized from ethyl acetate-chloroform to obtain 2.9 g of 6-[4-(2-hydroxy-2-phenylpropyl)-1-piperazinylcarbonyl]-3,4-dihydrocarbostyril. Colorless powdery substance. Melting point: 181°–184° C.

Next, this product was converted into a hydrochloride by using a concentrated hydrochloric acid-ethanol, then was recrystallized from methanol-ethanol to obtain 2.9 g of 6-[4-(2-hydroxy-2-phenylpropyl)-1-piperazinylcarbonyl]-3,4-dihydrocarbostyril hydrochloride. Colorless powdery substance. Melting point: 227°–229° C. (dec.)

By a procedure similar to that described in the above-mentioned Example 22, by using suitable starting materials respectively, there were prepared compounds of Examples 23–27 as shown in the following Table 2.

TABLE

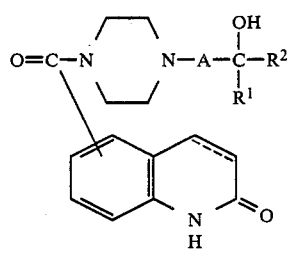

| Example No. | A | R¹ | R² | Substituted position of the side-chain | Carbon-carbon bond between 3- and 4- positions | Melting point (°C.) (Recrysallization solvent) | Crystal form | Salt |
|---|---|---|---|---|---|---|---|---|
| 23 | —CH$_2$— | -C$_6$H$_5$ | -C$_6$H$_5$ | 6 | Single bond | 187.5–191.0 (Ethyl acetate-chloroform) | Colorless prism-like crystals | — |
| 24 | —CH$_2$— | -C$_6$H$_5$ | -C$_6$H$_5$ | 6 | Single bond | 230–233 (dec.) (Ethyl acetate-methanol) | Colorless prism-like crystals | HCl |
| 25 | —CH$_2$— | CH$_3$ | -C$_6$H$_3$(OCH$_3$)$_2$ | 6 | Single bond | 195–197 (dec.) (Ethyl acetate-methanol) | Colorless powdery substance | HCl |
| 26 | —CH$_2$— | CH$_3$ | -C$_6$H$_4$-CH$_3$ | 6 | Single bond | 224–226 (dec.) (Ethyl acetate-methanol) | Colorless powdery substance | HCl |
| 27 | —CH$_2$— | CH$_3$ | -C$_6$H$_4$-OCH$_3$ | 6 | Single bond | Over 160 (dec.) (Ethyl acetate-methanol) | Colorless powdery substance | HCl |

EXAMPLE 28

3.6 Grams of 6-(1-piperazinylcarbonyl)-3,4-dihydrocarbostyril was dispersed in 40 ml of dimethylformamide, then to this suspension were added 4 g of geranyl bromide and 5.1 ml of triethylamine, and the whole mixture was stirred at room temperature for 3 hours. After the reaction was finished, the reaction mixture was poured in water and extracted with chloroform. The chloroform layer was washed with water and dried with magnesium sulfate. Chloroform was removed by evaporation under reduced pressure. The residue thus obtained was crystallized from diethyl ether, then dispersed in 20 ml of ethanol and converted into hydrochloride by adding 1.3 ml of concentrated hydrochloric acid. Recrystallization from ethanol-water to obtain 1.8 g of 6-(4-genranyl-1-piperazinylcarbonyl)-3,4-dihydrocarbostyril.hydrochloride. monohydrate. Colorless needle-like crystals. Melting point: 265°–266° C. (dec.)

EXAMPLES 29–46

By a method similar to that described in Example 28, and by using a suitable starting material, there were prepared compounds of Examples 1–27 and 29–46 as shown in Table 3 as follows.

TABLE 3

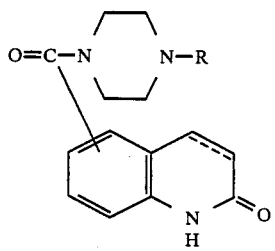

| Example No. | R | Substituted position of the side-chain in carbostyril skeleton | Melting point (°C.) (Recrystallization solvent) | Crystal form | Salt |
|---|---|---|---|---|---|
| 29 | (farnesyl-type chain) | 6 | 253 (dec.) (Ethanol-water) | Colorless powdery substance | HCl·½-H$_2$O |
| 30 | (geranyl-type chain) | 6 | 230–232 (dec.) (Ethanol-water) | Colorless powdery substance | (COOH)$_2$ |
| 31 | CH$_3$CH$_2$CH=CH–C$_6$H$_5$ | 6 | 232.5–240 (dec.) (Ethanol) | Colorless powdery crystals | HCl·H$_2$O |
| 32 | CH$_3$CH$_2$CH$_2$CH=CH–C$_6$H$_5$ | 6 | 259–265 (dec.) (Ethanol-water) | Colorless prism-like crystals | HCl |
| 33 | CH$_3$CH$_2$C≡C–C$_6$H$_5$ | 6 | 235–240 (dec.) (Ethanol) | Colorless prism-like crystals | HCl |
| 34 | CH$_3$CH$_2$CH$_2$CH=CH–C$_6$H$_4$–SCH$_3$ | 6 | 255–256 (dec.) (Ethanol-water) | Colorless powdery substance | HCl·H$_2$O |
| 35 | CH$_3$CH$_2$CH$_2$CH=CH–C$_6$H$_4$–S(O)CH$_3$ | 6 | 224–225 (dec.) (Ethanol-water) | Colorless powdery substance | HCl·H$_2$O |
| 36 | C$_6$H$_5$– | 6 | 200–201 (Isopropanol) | Colorless needle-like crystals | — |
| 37 | 2-H$_3$CO–C$_6$H$_4$– | 6 | 226–227.5 (dec.) (Ethanol-chloroform) | Colorless powdery substance | — |
| 38 | 2-CH$_3$-3-Cl-C$_6$H$_3$– | 6 | 210–211 (Methanol) | Colorless powdery substance | — |

TABLE 3-continued

[Structure: piperazine-carbonyl substituted carbostyril]

| Example No. | R | Substituted position of the side-chain in carbostyril skeleton | Melting point (°C.) (Recrystallization solvent) | Crystal form | Salt |
|---|---|---|---|---|---|
| 39 | 2-Cl-phenyl | 6 | 134–136 (Ethanol) | Colorless powdery substance | — |
| 40 | 4-F-phenyl | 6 | 179–181 (Ethanol) | Light yellow granular substance | — |
| 41 | 3-Cl-phenyl | 6 | 198–199 (Ethanol) | Colorless needle-like crystals | — |
| 42 | 4-OCH$_3$-phenyl | 6 | 226–228 (Ethanol) | Colorless powdery substance | — |
| 43 | 2,3-di-OCH$_3$-phenyl | 6 | 204–206 (dec.) (Methanol) | Colorless flake-like crystals | — |
| 44 | 4-SCH$_3$-phenyl | 6 | 238–239 (Methanol-chloroform) | Colorless powdery substance | — |
| 45 | 4-S(O)CH$_3$-phenyl | 6 | 240–242 (dec.) (Methanol) | Colorless powdery substance | — |
| 46 | CH$_3$-C(phenyl)=CH-CH$_2$-CH$_3$ | 6 | 267–269 (dec.) (Ethanol-water) | Colorless plate-like crystals | HCl |

EXAMPLE 47

127 Milligrams of succinimide 3,4-dihydrocarbostyril-6-carbostyril-6-carboxylate and 117 mg of geranyl-piperazine were dissolved in 2 ml of dimethylformamide, and the solution was stirred for 24 hours. To the reaction mixture was added a certain amount of water and then extracted with chloroform, the chloroform layer was washed with water and an aqueous solution saturated with sodium chloride. Then the chloroform extract was dried with anhydrous sodium sulfate, and the solvent was removed by evaporation under reduced pressure. The residue thus obtained was crystallized by adding diethyl ether, and the crystals formed were dispersed in 20 ml of ethanol, then converted into hydrochloride by adding 1.3 ml of concentrated hydrochloric acid. Recrystallized from ethanol-water to obtain 132 mg of 6-(4-geranyl-1-Piperazinyl)-3,4-dihydrocarbostyril.hydrochloride.mono-hydrate. Colorless needle-like crystals. Melting point: 265°-266° C. (dec.)

By using method similar to that described in Example 47, and by using a suitable starting material, there were prepared compounds of Examples 1-27 and 29-46.

EXAMPLE 48

2.62 Grams of 6-morpholinocarbonyl-3,4-dihydrocarbostyril and 10 g of aniline were placed in a sealed tube and heated at 170°-200° C. for 5 hours. Excess aniline was removed by evaporation under reduced pressure, then the residue thus obtained was purified by means of silica gel column chromatography. Recrystallized from isopropanol to obtain 0.32 g. of 6-(4-phenyl-1-piperazinylcarbonyl)-3,4-dihydrocarbostyril. Colorless needle-like crystals. Melting point: 200°-201° C.

By using a method as described in Example 48, and by using a suitable starting material, there were prepared compounds of Examples 1-27, 28-35 and 37-46.

EXAMPLE 49

A mixture consisting of 10 g of 6-[bis-(2-hydroxyethyl)aminocarbonylp9 -3,4-dihydrocarbostyril, 2.5 g of aniline and 7.6 g of polyphosphoric acid was heated at 160°-170° C. for about 6 hours to react. The reaction mixture was let cooled, then about 500 ml of water was added dropwise to the reaction mixture to dissolve. The solution was neutralized with 48%-sodium hydroxide solution, then extracted with chloroform. The chloroform extract was dried with anhydrous potassium carbonate, and chloroform was removed by evaporation. The residue thus obtained was recrystallized from isopropanol to obtain 6.4 g of 6-(4-phenyl-1-piperazinylcarbonyl)-3,4-dihydrocarbostyril. Colorless needle-like crystals. Melting point: 200°-201° C.

By using a method similar to that described in Example 49, and by using a suitable starting material, there were prepared compounds of Examples 1-27, 28-35 and 37-46.

EXAMPLE 50

A mixture consisting of 15.9 g of 6-[bis-(2-chloroethyl)aminocarbonyl]-3,4-dihydrocarbostyril, 5.5 g of aniline and 70 ml of methanol was refluxed for 15 hours. After cooled the reaction mixture, 3.06 g of sodium carbonate was added to the reaction mixture and the reaction mixture was further refluxed for 8 hours. The reaction mixture was cooled and crystals precipitated in the reaction mixture were collected by filtration, and recrystallized from isopropanol to obtain 6.3 g of 6-(4-phenyl-1-piperazinylcarbonyl)-3,4-dihydrocarbostyril. Colorless needle-like crystals. Melting point: 200°-201° C.

By using a method similar to that described in Example 50, and using a suitable starting material, there were prepared compounds of Examples 1-27, 28-35 and 37-46.

EXAMPLE 51

1.0 Gram of 6-carboxy-3,4-dihydrocarbostyril, 1.3 g of DCC (dicyclohexylcarbodiimide) and 1.4 g of geranylpiperazine were suspended in 10 ml of dioxane, and the suspension was stirred at 60°-70° C. for 5 hours. After the reaction was finished, the solvent was removed from the reaction mixture by evaporation, then to the residue thus obtained was added a certain amount of diethyl ether and the crystals formed were removed by filtration. The mother liquor was concentrated, and the residue thus obtained was dissolved by adding chloroform, the chloroform solution was washed with water and an aqueous solution saturated with sodium chloride. The chloroform solution was dried with anhydrous sodium sulfate, then the solvent was removed by evaporation. To the residue thus obtained was added 20 ml of ethanol, and converted into hydrochloride with 1.3 ml of concentrated hydrochloric acid. Recrystallized from ethanol-water to obtain 340 mg of 6-(4-geranyl-1-piperazinylcarbonyl)-3,4-dihydrocarbostyril.hydrochloride. monohydrate. Colorless needle-like crystals. Melting point: 265°-266° C. (dec.).

By using a method similar to that described in Example 49, and by using a suitable starting material, there were prepared compounds of Examples 1-27 and 29-46.

EXAMPLE 52

1.6 Grams of 6-carboxy-3,4-dihydrocarbostyril and 0.8 ml of triethylamine were suspended in 10 ml of THF (tetrahydrofuran), to this suspension was added dropwise 10 ml of THF solution containing 1.0 g of diethyl chlorophosphate at room temperature under stirring, then the whole mixture was stirred at room temperature for 3 hours. Then to this reaction mixture was added dropwise 10 ml of THF solution containing 1.4 g of geranylpiperazine, then the whole reaction mixture was stirred further at room temperature for 10 hours. After the reaction was finished, the crystals formed in the reaction mixture were removed by filtration, then the mother liquor was concentrated. To the residue thus obtained was added an aqueous solution saturated with sodium bicarbonate, then extracted with chloroform. The organic layer was washed with water and an aqueous solution saturated with sodium chloride, and dried with anhydrous sodium sulfate, then the solvent was removed by evaporation. The residue was converted into hydrochloride by adding ethanol-concentrated hydrochloric acid. Recrystallized from ethanol-water to obtain 1.08 g of 5-(4-geranyl-1-piperazinylcarbonyl)-3,4-dihydrocarbostyril.hydrochloride.monohydrate. Colorless needle-like crystals. Melting point: 265°-266° C. (dec.).

By a method similar to that described in Example 52, and by using a suitable starting material, there were prepared compounds of Examples 1-27 and 29-46.

EXAMPLE 53

34.5 Grams of 6-carboxycarbostyril and 31 ml of triethylamine were dissolved in 350 ml of DMF (dimethyl sulfoxide), and to this solution was added dropwise a solution containing 28 ml of isobutyl chloroformate and 14 ml of DMF at room temperature under stirring. After stirred at room for 1 hour, 21 ml of DMF solution containing 46.7 g of geranylpiperazine was added dropwise thereto, and the whole mixture was stirred at room temperature for 10 hours. The reaction mixture was poured in an aqueous solution saturated with sodium bicarbonate, then extracted with chloroform. The chloroform layer was washed with water, an aqueous solution saturated with sodium chloride in this order, then dried with anhydrous sodium sulfate. The solvent was removed by evaporation under reduced pressure, the residue thus obtained was crystallized by adding diethyl ether, and the crystals were collected by filtration. The crystals were dissolved in ethanol and was converted into hydrochloride by adding concentrated hydrochloric acid. The crude crystals obtained were recrystallized from ethanol-water to obtain 32 g of 6-(4-geranyl-1-piperazinylcarbonyl)carbostyril hydrochloride monohydrate. Colorless needle-like crystals. Melting point: 265°–266° C. (dec.).

By using a method similar to that described in Example 53, and using a suitable starting material, there were prepared compound of Examples 1–27 and 29–46.

EXAMPLE 54

Into 100 ml of ethanol, 2.0 g of 6-ethoxycarbonyl-3,4-dihydrocarbostyril, 0.5 g of sodium ethylate and 2.02 g of geranylpiperazine were added and the whole mixture was placed in an autoclave and reacted at 140°–150° C. for 6 hours. After the reaction was finished, the reaction mixture was cooled and concentrated under reduced pressure. The residue was dissolved in 200 ml of chloroform, then washed with 1%-potassium carbonate aqueous solution, diluted hydrochloric acid and water in this order, then dried with anhydrous sodium sulfate. The solvent was removed by evaporation, the residue was converted into hydrochloride by adding ethanol-concentrated hydrochloric acid, then recrystallized from ethanol-water to obtain 318 mg of 6-(4-geranyl-1-piperazinylcarbonyl)-3,4-dihydrocarbostyril hydrochloride monohydrate. Colorless needle-like crystals. Melting point: 265°–266° C. (dec.).

By using a method similar to that described in Example 54, and by using a suitable starting material, there were prepared compounds of Examples 1–27 and 29–46.

EXAMPLE 55

1.9 Grams of 6-carboxy-3,4-dihydrocarbostyril was suspended in 200 ml of methylene chloride, then 2 ml of pyridine was added thereto. The mixture was kept at 0°–20° C., under stirring condition, 1.4 g of thionyl chloride was added dropwise. After the dropwise addition was finished, the whole reaction mixture was stirred for 1 hour at the same temperature, and 10 ml of methylene chloride containing 2.19 g of geranylpiperazine was added dropwise. After the dropwise addition was finished, the reaction mixture was stirred at room temperature for 4 hours. The reaction mixture was thoroughly washed with an aqueous solution of potassium carbonate, then further washed with water and diluted hydrochloric acid, then dried with anhydrous sodium sulfate, and the solvent was removed by evaporation. The residue thus obtained was converted into hydrochloride by adding ethanol-hydrochloric acid, and recrystallized from ethanol-water to obtain 343 mg of 6-(4-geranyl-1-piperazinylcarbonyl)-3,4-dihydrocarbostyril hydrochloride.monohydrate. Colorless needle-like crystals. Melting point: 265°–266° C. (dec.).

By using a method similar to that described in Example 55, and by using a suitable starting material, there were prepared compounds of Examples 1–27 and 29–46.

Examples of pharmaceutical preparations each of which containing carbostyril derivative represented by the general formula (1) according to the present invention are shown as follows.

| Example of Preparation of Tablets - 1 | |
|---|---|
| 6-[4-(3-Phenyl-3-hydroxypropyl)-1-piperazinylcarbonyl]-3,4-dihydrocarbostyril | 5 mg |
| Starch | 132 mg |
| Magnesium stearate | 18 mg |
| Lactose | 45 mg |
| Total | 200 mg |

By a method according to usual manner, there were prepared tablets having the above-mentioned formulation in one tablet.

| Example of Preparation of Tablets - 2 | |
|---|---|
| 6-[4-(4-Phenyl-4-hydroxybutyl)-1-piperazinylcarbonyl]-3,4-dihydrocarbostyril | 10 mg |
| Starch | 127 mg |
| Magnesium stearate | 18 mg |
| Lactose | 45 mg |
| Total | 200 mg |

By a method according to usual manner, there were prepared tablets having the above-mentioned formulation in one tablet.

| Example of Preparation of Tablets - 3 | |
|---|---|
| 6-[3-(4-Methylphenyl)-3-hydroxypropyl)-1-piperazinylcarbonyl]carbostyril monohydrochloride | 5 mg |
| Starch | 132 mg |
| Magnesium stearate | 18 mg |
| Lactose | 45 mg |
| Total | 200 mg |

By a method according to usual manner, there were prepared tablets having the above-mentioned formulation in one tablet.

| Example of Preparation of Tablets - 4 | |
|---|---|
| 6-(4-Geranyl-1-piperazinylcarbonyl)-3,4-dihydrocarbostyril | 5 mg |
| Starch | 132 mg |
| Magnesium stearate | 18 mg |
| Lactose | 45 mg |
| Total | 200 mg |

By a method to usual manner, there were prepared tablets having the above-mentioned formulation in one tablet.

| Example of Preparation of Tablets - 5 | |
|---|---|
| 6-(4-Farnesyl-1-piperazinylcarbonyl)-3,4-dihydrocarbostyril | 10 mg |
| Starch | 127 mg |
| Magnesium stearate | 18 mg |
| Lactose | 45 mg |
| Total | 200 mg |

By a method according to usual manner, there were prepared tablets having the above-mentioned formulation in one tablet.

| Example of Preparation of Tablets - 6 | |
|---|---|
| 6-[4-(4-Phenyl-3-butenyl)-1-piperazinylcarbonyl]-3,4-dihydrocarbostyril monohydrochloride | 5 mg |
| Starch | 132 mg |
| Magnesium stearate | 18 mg |

| Example of Preparation of Tablets - 6 | |
| --- | --- |
| Lactose | 45 mg |
| Total | 200 mg |

By a method according to usual manner, there were prepared tablets having the above-mentioned formulation in one tablet.

| Example of Preparation of Injection - 1 | |
| --- | --- |
| 6-[4-(2-Phenyl-2-hydroxyethyl)-1-piperazinylcarbonyl]-3,4-dihydrocarbostyril | 500 mg |
| Polyethylene glycol (Molecular weight: 4,000) | 0.3 g |
| Sodium chloride | 0.9 g |
| Polyoxyethylene sorbitan monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

The above-mentioned methyl p-hydroxybenzoate, propyl p-hydroxybenzoate, sodium metabisulfite and sodium chloride were dissolved in distilled water for injection at 80° C. under stirring. Thus obtained solution was cooled to 40° C., then 6-[4-(2-phenyl-2-hydroxyethyl)-1-piperazinylcarbonyl]-3,4-dihydrocarbostyril, polyethylene glycol and polyoxyethylene sorbitan monooleate were dissolved in this order in the cooled solution. Then to this solution was added further distilled water for injection so as to adjust the final volume and then sterilized by sterile filtration with a suitable filter paper. One milliliter each of thus obtained solution was filled in an ampoule separately to make injection preparation.

| Example of Preparation of Injection - 2 | |
| --- | --- |
| 6-(4-Geranyl-1-piperazinylcarbonyl)-3,4-dihydrocarbostyril | 500 mg |
| Polyethylene glycol (Molecular weight: 4,000) | 0.3 g |
| Sodium chloride | 0.9 g |
| Polyoxyethylene sorbitan monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

The above-mentioned methyl p-hydroxybenzoate, propyl p-hydroxybenzoate, sodium metabisulfite and sodium chloride were dissolved in distilled water for injection at 80° C. under stirring. Thus obtained solution was cooled to 40° C., then 6-(4-geranyl-1-piperazinylcarbonyl)-3,4dihydrocarbostyril, polyethylene glycol and polyoxyethylene sorbitan monooleate were dissolved in this order in the cooled solution. Then to this solution was added further distilled water for injection so as to adjust the final volume and then sterilized by sterile filtration with a suitable filter paper. One milliliter each of thus obtained solution was filled in an ampoule separately to make injection preparation.

Pharmacological Test

Pharmacological activities of carbostyril derivatives represented by the general formula (1) according to the present invention were determined by test method as explained below with the test results as follows.

(1) Test compounds (1) 6-{4-[3-(4-Methoxyphenyl)-3-hydroxypropyl]-1-piperazinylcarbonyl}-3,4-dihydrocarbostyril monohydrochloride (2) 6-[4-(2-Phenyl-2-hydroxyethyl)-1-piperazinyl-carbonyl]-3,4-dihydrocarbostyril monohydrochloride ½-hydrate (3) 6-{4-[3-(4-Methylphenyl)-3-hydroxypropyl]-1-piperazinylcarbonyl}carbostyril monohydrochloride (4) 6-{4-[3-Chlorophenyl)-2-hydroxyethyl]-1-piperazinylcarbonyl}-3,4-dihydrocarbostyril monohydrochloride (5) 6-[4-(3-Phenyl-3-hydroxypropyl)-1-piperazinylcarbonyl]-3,4-dihydrocarbostyril monohydrochloride (6) 6-[4-(4-Phenyl-4-hydroxybutyl)-1-piperazinylcarbonyl]-3,4-dihydrocarbostyril monohydrochloride (7) 6-(4-Geranyl-1-piperazinylcarbonyl)-3,4-dihydrocarbostyril (8) 6-[4-(2-Methoxyphenyl)-1-piperazinylcarbonyl]-3,4-dihydrocarbostyril (9) 6-[4-(2-Methyl-3-chlorophenyl)-1-piperazinylcarbonyl]-3,4-dihydrocarbostyril

(10) 6-[4-(2-Chlorophenyl)-1-piperazinylcarbonyl]-3,4-dihydrocarbostyril

(11) 6-[4-(3-Phenyl-2-propenyl)-1-piperazinylcarbonyl]-3,4-dihydrocarbostyril

(12) 6-[4-(4-Phenyl-3-butenyl)-1-piperazinylcarbonyl]-3,4-dihydrocarbostyril (2) Test method Adult mongrel dog of either sex, weighing 8–13 kg, was anesthetized with sodium pentobarbital at the rate of 30 mg/kg by intravenous administration. After another intravenous administration of sodium heparin at the rate of 1,000 U/kg, the test dog was killed by bleeding. The heart of the test dog was taken out by excision, and the sample of the heart was essentially consisting of the anterior papillary muscle and the venticular septum. The sample of the excised heart was cannulated at the anterior septal artery and perfused with the blood supplied from a donor dog at the constant blood pressure of 100 mm-Hg. The dog used as the donor was weighing 18–27 kg, and was anesthetized with pentobarbital sodium at the rate of 30 mg/kg by intravenous administration, and further treated with intravenous administration of sodium heparin at the rate of 1,000 U/kg. The papillary muscle was stimulated by rectangular pulse wave at about 1.5 times the threshold voltage (0.5–3 volts) with 5 milliseconds duration on the fixed rate of 120 beats/minute through a bipolar pacing electrodes. The papillary muscle was loaded with the weight of about 1.5 grams, and the tension developed by the papillary muscle was measured by a strain-gauge transducer. The blood flow through the anterior septal artery was measured by an electromagnetic flow meter. The developed tension and the blood flow were recorded on charts with an ink-writing recorder. The details of this test method was reported in an article written by Endoh and Hashimoto: American Journal of Physiology, Vol. 218, pp. 1459–1463 (1970).

The test compound was intraarterially administered in the amount of 10–30 microliters in 4 seonds.

The inotropic effects of the test compounds were expressed as a percentage of the developed tension before the intraarterially administration of the test compound.

The effect of the test compound on the blood flow were expressed as a difference (milliliter/minute) of the values before and after the intraarterially administration of the test compound.

The test results are shown in the following Tables 4 and 5. In Table 5, the test results are shown as the ratios of the data obtained from the test compounds to the data obtained from Amrinone [3-amino-5-(4-pyridinyl)-2(1H)-pyridinone] used as a reference compound.

TABLE 4

| Test compound No. | Dosage | Change of arterial muscle contriction (%) | Change of blood flow in coronary artery (ml/minute) |
|---|---|---|---|
| 1 | 1 μm | 28.8 | 4.0 |
| 2 | 1 μm | 92.6 | 2.5 |
| 3 | 1 μm | 52.5 | 3.5 |
| 4 | 1 μm | 58.5 | 5.0 |
| 5 | 1 μm | 47.0 | 5.0 |
| 6 | 1 μm | 40.0 | 5.0 |

TABLE 5

| Test compound No. | Dosage | Change of arterial muscle contriction, (Ratio of values obtained from test compound/Amrinone) | Change of blood flow in coronary artery (Ratio of values obtained from test compound/Amrinone) |
|---|---|---|---|
| 7 | 1 μm | 0.75 | 3.18 |
| 8 | 300 nm | 1.48 | 1.00 |
| 9 | 300 nm | 0.72 | 1.00 |
| 10 | 1 μm | 0.64 | 1.38 |
| 11 | 1 μm | 1.07 | 1.29 |
| 12 | 1 μm | 1.19 | 1.00 |

What is claimed is:

1. The carbostyril compound and salt thereof represented by the formula

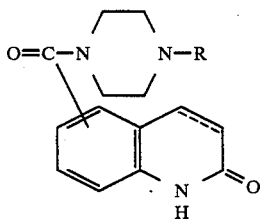

wherein R is an alkenyl group having 7 to 12 carbon atoms, and having 2 or 3 double bonds in the alkenyl chain, a phenyl-lower alkenyl group or phenyl-lower alkenyl group having, on the phenyl ring, lower alkylthio groups or lower alkylsulfinyl groups as substituents, a phenyl-lower alkynyl group, or a group of the formula

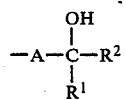

wherein A is a lower alkylene group; $R^1$ is a hydrogen atom, a lower alkyl group or a phenyl group; and $R^2$ is a phenyl group or a phenyl group having 1 to 3 substituents selected from the group consisting of a hydroxy group, a halogen atom, a lower alkyl group, a lower alkoxy group, a lower alkanoylamino group, a lower alkylthio group and a lower alkylsulfinyl group on the phenyl ring; and wherein the carbon-carbon bond between the 3- and 4-positions in the carbostyril skeleton is a single or double bond.

2. The carbostyril compound and salt thereof according to claim 1, wherein R is a group of the formula

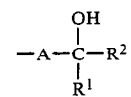

where in $R^1$ and $R^2$ are the same as defined in claim 1.

3. The carbostyril compound and salt thereof according to claim 1, wherein R is an alkenyl group having 7 to 12 carbon atoms and having 2 to 3 double bonds in the alkenyl chain.

4. The carbostyril compound and salt thereof according to claim 1, wherein R is a phenyl-lower alkenyl group or said group having, on the phenyl ring, lower alkylthio groups or lower alkylsulfinyl groups as substituents.

5. The carbostyril compound and salt thereof according to claim 1, wherein the substituted position of a side-chain of the formula

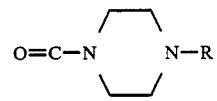

is the 6-position in the carbostyril skeleton, and the carbon-carbon bond between the 3- and 4-positions in the carbostyril skeleton is a single bond.

6. The carbostyril compound and salt thereof according to claim 2, wherein $R^1$ is a hydrogen atom.

7. The carbostyril compound and salt thereof according to claim 2, wherein $R^1$ is a lower alkyl group or a phenyl group.

8. The carbostyril compound and salt thereof according to claim 6, wherein the substituted position of a side-chain of the formula

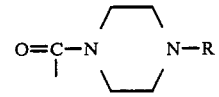

is 6-position in the carbostyril skeleton.

9. The carbostyril compound and salt thereof according to claim 7, wherein the substituted position of a side-chain of the formula

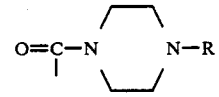

is 6-position in the carbostyril skeleton.

10. The carbostyril compound and salt thereof according to claim 3, wherein the carbon-carbon bond between 3- and 4-positions in the carbostyril skeleton is a single bond.

11. 6-[4-(2-Hydroxy-2-phenylethyl)-1-piperazinylcarbonyl]-3,4-dihydrocarobstyril.

12. 6-{4-[2-Hydroxy-2-(3-chlorophenyl)ethyl]-1-piperazinylcarbonyl}-3,4-dihydrocarbostyril.

13. 6-{4-[3-Hydroxy-3-(4-methylphenyl)propyl]-1-piperazinylcarbonyl}carbostyril.

14. 6-{4-[3-Hydroxy-3-(4-methoyphenyl)propyl]-1-piperazinylcarbonyl}-3,4-dihydrocarbostyril.

15. 6-{4-[3-Hydroxy-3-(4-methylphenyl)propyl]-1-piperazinylcarbonyl}-3,4-dihydrocarbostyril.

16. 6-{4-[3-hydroxy-3-(4-methylthiopheny)propyl]-1-piperazinylcarbonyl}-3,4-dihydrocarbostyril.

17. 6-(4-Geranyl-1-poperazinylcarbonyl)-3,4-dihydrocarbostyril.

18. A cardiotonic composition containing, as the active ingredient, a carbostyril compound or salt thereof represented by the formula (1) as claimed in claim 1, and a pharmaceutically acceptable carrier.

* * * * *

UNITED STATES PATENT AND TRADEMARK OFFICE
CERTIFICATE OF CORRECTION

PATENT NO. : 4,845,100

DATED : July 4, 1989

INVENTOR(S) : Atsushi Abiko et al.

It is certified that error appears in the above-identified patent and that said Letters Patent is hereby corrected as shown below:

In claim 14 at column 41, line 4, the term "4-methoyphenyl" should read --4-methoxyphenyl--.

Signed and Sealed this

Thirty-first Day of July, 1990

Attest:

HARRY F. MANBECK, JR.

*Attesting Officer*  *Commissioner of Patents and Trademarks*